United States Patent [19]

Mui

[11] 4,012,403

[45] Mar. 15, 1977

[54] SYNTHESIS OF MERCAPTO-SUBSTITUTED SILICON COMPOUNDS

[75] Inventor: Jeffrey Yick Pui Mui, Tarrytown, N.Y.

[73] Assignee: Union Carbide Corporation, New York, N.Y.

[22] Filed: Mar. 18, 1976

[21] Appl. No.: 667,987

Related U.S. Application Data

[63] Continuation-in-part of Ser. No. 611,676, Sept. 9, 1975, abandoned, which is a continuation of Ser. No. 216,728, Jan. 10, 1972, abandoned.

[52] U.S. Cl. .................. 260/448.8 R; 260/448.2 E; 260/448.2 N; 260/609 R
[51] Int. Cl.² .......................................... C07F 7/18

[58] Field of Search ............. 260/448.8 R, 448.2 E, 260/448.2 N, 609 A

[56] References Cited

UNITED STATES PATENTS

| | | | |
|---|---|---|---|
| 2,230,390 | 2/1941 | Signaigo | 260/609 A |
| 3,565,937 | 2/1971 | Berger | 260/448.8 R |

*Primary Examiner*—Paul F. Shaver
*Attorney, Agent, or Firm*—George A. Skoler

[57] ABSTRACT

This invention relates to a method of reducing $\beta$-cyanoethyltrialkoxysilane to the corresponding mercaptopropyltrialkoxysilane by reaction with sulfur.

1 Claim, No Drawings

SYNTHESIS OF MERCAPTO-SUBSTITUTED SILICON COMPOUNDS

This is a continuation-in-part of copending U.S. application Ser. No. 611,676, filed Sept. 9, 1975 now abandoned, which is, in turn, a continuation of U.S. application Ser. No. 216,728, filed Jan. 10, 1972 now abandoned.

This invention relates to a novel process for making mercaptopropylalkoxysilanes. The process of this invention involves converting β-cyanoethyltrialkoxysilane in a simple manner to yield essentially quantitative amounts of mercaptopropyltrialkoxysilane.

Mercapto substituted silicon compounds are known in the art. They have been made by essentially two processes. One involves the addition of hydrogen sulfide to an ethylenically unsaturated radical bonded directly to silicon. This is illustrated in the reaction of hydrogen sulfide with a vinyl substituted silane. Another method for the manufacture of mercapto substituted silicon compounds involves the reaction of sodium mercaptide with a chloroalkyl silicon compound. Both methods suffer from a number of processing difficulties. For example, the reaction of hydrogen sulfide with the ethylenically unsaturated silicon compound suffers from the requirement that a large excess of hydrogen sulfide must be employed in order to effect the reaction. Excesses greater than 400% of the stoichiometric quantity necessary to form the mercapto substitution are required. In addition, the reaction also causes the formation of a relatively large quantity of the sulfide of the ethylenically unsaturated silicon compound. Yields of such sulfide can run as high as about 25 weight % of the reaction product.

With respect to the reaction between sodium mercaptide and the chloro alkyl silicon compounds to form the mercaptans, a number of processing difficulties are present. For example, the yield of chloroalkyl silicon compound that one can obtain is relatively low, particularly when making a chloroalkyl silicon compound such as a gamma-chloropropyl silicon compound by the reaction of allyl chloride and a silicon hydride. Usually, the yield of desired chlorinated product does not exceed about 60 weight %, based on the weight of the starting silicon hydride material. In addition, since sodium mercaptide is a solid, a substantial quantity of solvent is needed in the process. Usually the solvent is methanol and the methanol content is about 70 weight % of the sodium mercaptidemethanol mixture. The reaction between sodium mercaptide and chlorinated alkyl silicon compound results in the formation of sodium chloride. Sodium chloride is a corrosive material and its removal adds to the cost of the process.

There is described herein a process which essentially avoids the type of problems characterized above. This process achieves practically quantitative yields of the mercaptopropyltrialkoxysilane utilizing relatively inexpensive starting materials. The process of this invention involves the reaction between a β-cyanoethyltrialkoxysilane, sulfur (desirably in elemental form, but also may be in the form of sulfur containing compounds) and hydrogen in the presence of sulfide or polysulfide catalysts of transition metals. This reaction results in the abstraction of the nitrogen atom of the nitrile as ammonia, and the addition to the carbon radical to which the nitrogen had been attached, of a mercapto group formed by the composition of elemental sulfur in the presence of hydrogen. The reaction achieves high yields of the corresponding mercaptopropyltrialkoxysilane.

The thiol conversion of alkyl cyanides is known in the art. This process is illustrated in U.S. Pat. No. 2,230,390. However, there has been no previous disclosure concerning the reductive thiolation of a cyanoalkyl hydrolyazble silane. The instant disclosure teaches that β-cyanoethyltrialkoxysilane can be successfully reduced to provide a high yield of mercaptan product.

Examples 1–4 demonstrate the variation in yields which can be obtained in a comparison of the reductive thiolation of cyanomethyl-, cyanoethyl-, and cyanopropylalkoxysilanes at pressurization with hydrogen of 800 to 950 psi. Example 2 shows that β-cyanoethyltrialkoxysilane can be successfully reduced to provide a high yield of product at low hydrogen pressurization (950 psi). In contrast, in this hydrogen pressurization range significantly lower yields of product are obtained in the thiolation of cyanomethyl- and cyanopropylalkoxysilanes. The results of such a comparison are summarized below in Table I.

TABLE I

| Example No. | Reactant | Product | % Product in Final Composition | % Starting Material in Final Comp. | Other Compounds in Final Composition Formula | % in Final Comp. |
|---|---|---|---|---|---|---|
| 1 | $(EtO)_3SiCH_2CN$ | $(EtO)_3SiCH_2CH_2SH$ | 0.8% | ND[4] | $C_2H_5SH$ | 15.8% |
| | | | | | $(EtO)_4Si$ | 62.6% |
| | | | | | $(EtO)_3SiOSi(OEt)_3$ | 12.5% |
| | | | | | $(EtO)_3SiOSi(OEt)_2OSi(OEt)_3$ | 3.2% |
| | | | | | Heavies[1] | 2.8% |
| | | | | | Unknowns | 2.4% |
| 2 | $(EtO)_3SiCH_2CH_2CN$ | $(EtO)_3SiCH_2CH_2CH_2SH$ | 68.7% | 13.2% | $(EtO)_4Si$ | 0.9% |
| | | | | | $(EtO)_3SiCH_2CH_2CH_3$ | 0.8% |
| | | | | | Heavies[1] | 16.5% |
| 3 | $\begin{array}{c}CH_3\\|\\(EtO)_2SiCH_2CH_2CH_2CN\end{array}$ | $\begin{array}{c}CH_3\\|\\(EtO)_2SiCH_2CH_2CH_2CH_2SH\end{array}$ | 24.7% | 59.9% | $\begin{array}{c}CH_3\quad\quad O\\|\quad\quad\quad\|\\(EtO)_2SiCH_2CH_2CH_2COEt\end{array}$ | 8.4% |
| | | | | | Heavies[1] | 6.9% |
| 4[3] | $CH_3CN$ | $C_2H_5SH$ | 54.1% | 6.9% | $H_2S$ and $NH_3$ | 9.7% |
| | | | | | $CH_3COOC_2H_5$ | 11.3% |
| | | | | | $CH_3CONH_2$ | 13.5% |
| | | | | | Unknowns | 4.5% |

[1]Hydrolysis products
[2]Identical to amounts contained in starting material
[3]Control experiment
[4]Not determined It should be noted that in Example 1 the thiolation of cyanomethyltriethoxysilane resulted in the formation of appreciable percentages of ethyl mercaptan and tetraethylsilicate. This would indicate that in the thiolation of cyanomethyltriethoxysilane cleavage of the Si-C bond occurred in addition to the thiolation of the nitrile function.

It has been found most surprising that the reductive thiolation of β-cyanoethyltrialkoxysilane achieved a significantly higher yield of mercaptan product than could be obtained by the reductive thiolation of γ-cyanopropylmethyldiethoxysilane, indicating that the position of the silicon atom plays an important role in such a process. This conclusion is reinforced by the results of the thiolation of cyanomethyltriethoxysilane shown in Example 1.

The catalyst which is employed to effect the present invention may be any of the sulfide and polysulfide transition metal hydrogenation catalysts, such as, for example, cobalt sulfide and polysulfide, nickel sulfide and polysulfide, titanium sulfide and polysulfide, rhenium sulfide and polysulfide, molybdenum sulfide and polysulfide, and the like.

The temperature at which the reaction may be carried out can be as low as about 50° C. to about 300° C., though it is preferred that the reaction be carried out at a temperature of at least about 150° C. to about 250° C.

A significant advantage of the process of this invention is that it may be carried out in the absence of any solvents and any other material other than those described above, to wit, the cyano substituted silicon compound, sulfur, hydrogen and the catalyst. Thus, the process of this invention results in the neat formation of the desired mercapto product as the only solid or liquid product of the reaction and the only other product of the reaction is ammonia which is easily vaporized from the reaction product. Typically, the yields obtainable of the desired mercapto product from the process of this invention range from about 65 mole % to about 95 mole %, based upon the number of moles of the starting cyano substituted silicon compound. Thus, distinctive from the aforementioned prior art processes, the process of this invention provides high yields, essentially no liquid or solid by-products of any consequential amounts, and does not require the employment of solvents from which the product of the reaction must be separated.

The amount of hydrogen present in the reaction should be sufficient to provide at least three moles of hydrogen for each mole of cyano-substitution in the silicon compound. Stated in another manner, there should be provided in the reaction at least one mole of sulfur and three moles of hydrogen for every cyano group which is present in the silicon compounds when converting each cyano group to a mercapto group.

The condition of the silicon compound, that is, its physical state, is not critical to the practice of this invention though it is preferred that the silicon compound which is being treated be in the liquid or gaseous state during the reaction. Thus, the only cyano-substituted compounds which are excluded by the process of this invention are those which are in the cross-linked infusable condition. If the composition is capable of being rendered fluid in any manner, such as by increasing the temperature to reduce the viscosity to a workable level of, for example, one million centipoises determined at 50° C., then it is employable for conversion according to the process of this invention into a mercapto substituted silicon compound.

The amount of catalyst which is employed in the practice of this invention may range from an amount as low as about 0.001 to about 10 weight %., based on the weight of the starting reactants, that is, the cyano silicon compound, sulfur and hydrogen. Preferably the amount employed ranges from about 0.1 to about 5 weight %, same basis.

The process of this invention is usually practiced in a pressure vessel such as an autoclave or other types of pressure reactors. The catalyst is typically a solid and is employed as particulated material distributed within the pressure reactor. Any of the known methods for uniform distribution of a solid particulate catalyst throughout a reactor wherein the reaction is effected at an elevated temperature, such as described above, may be employed in the practice of this invention. Usually, the process is carried out at pressures equivalent to at least atmospheric pressure, such as a pressure of at least about 15 pounds per square inch up to about the limits of the pressurized vessel. For example, pressures ranging in the tens of thousands may be employed, and as the pressure is increased the reaction rate is increased. In practice, it is preferred that the reaction be carried out at a hydrogen pressure of at least about 900 pounds per square inch to about 2000 pounds per square inch.

The effects of pressure in the reactor were noted. In the reductive thiolation of β-cyanoethyltrialkoxysilane with sulfur and hydrogen using cobalt polysulfide as catalyst high yields of the corresponding mercaptopropyltrialkoxysilane at 200° C. and 1800 p.s.i.g. of hydrogen pressure were obtained. However, as the hydrogen pressure in the reactor was lowered to below 1000 p.s.i.g. an unexpected side reaction occurred. This side reaction produced tetraethylorthosilicate, $Si(Et)_4$, when beta-cyanoethyltriethoxysilane was thiolated. The effect of hydrogen pressure on the reductive thiolation of beta-cyanoethyltriethoxysilane was studied and the following summarized these results.

| Experiment | Hydrogen Pressure Range, p.s.i.g. | $(EtO)_3Si(CH_2)_3SH/Si(OEt)_4$ Molar Ratio Obtained |
|---|---|---|
| 1 | 500 – 900 | 1/3.2 |
| 2 | 900 – 1200 | 1/0.77 |
| 3 | 1200 – 1800 | 1/0.082 |
| 4 | 1800 – 2600 | 1/0.036 |

These four experiments were carried out under the same conditions at 200° C. for 5 hours. Thus, as the hydrogen pressure was lowered to less than about 1000 p.s.i.g., the amount of $Si(OEt)_4$ produced became significant. The mechanism in which tetraethylorthosilicate was produced was not resolved. However, this undesirable side reaction is avoided easily by (1) using a hydrogenated form of sulfur, such as, hydrogen sulfide, $H_2S$, instead of sulfur and (2) using rhenium heptasulfide, $Re_2S_7$, as a co-catalyst with cobalt polysulfide. The rhenium heptasulfide cocatalyst was used in about 0.2 weight percent based on total starting material charged. Experimental procedures are illustrated in Examples 5–9 below.

The following illustrates specific modes for the practice of this invention. It is not intended that such act to limit this invention in any way.

In the examples, the symbols and abbreviations used have the following meanings:

g. = grams psi = pounds per square inch
Et = ethyl
% = percent by weight
ml. = milliliters
mm. = millimeters
p.s.i.g. = pounds per square inch gauge

EXAMPLE 1

Into a 300 ml. high pressure reaction vessel were charged 41.0 g (0.20 mole) of cyanomethyltriethoxysilane and 18.3 g of $CoS_3$/NaCl/EtOH (1.03 g or 6.6 millimoles of $CoS_3$). The molar ratio of nitrile to catalyst was 30:1. The reactor was sealed and 6.9 g (0.20 mole) of hydrogen sulfide were added to the chilled vessel, followed by pressurization to 850 psi (approx. 0.5 mole) with hydrogen. The reactor was heated to 200°–215° C for 5 hours with agitation. The maximum pressure achieved was 1900 psi, slowly dropping to 1600 psi at 200°. The final pressure at ambient temperature was 400 psi. After cooling, the composition of the product was analyzed by vapor phase chromatography. The product composition is given in Table I, supra.

EXAMPLE 2

Into a 300 ml high pressure reaction vessel were charged 50 g (0.23 mole) of β-cyanoethyltriethoxysilane and 22.3 g of 5.61 wt% $CoS_3$ in ethanol (1.25 g of $CoS_3$). The molar ratio of nitrile to catalyst was 29:1. The reactor was sealed, cooled in Dry Ice, and 8.5 g (0.25 mole) of $H_2S$ were added. The reactor was then pressurized to 950 psi (approx. 0.6 mole) with hydrogen. The vessel was heated with agitation to a temperature of 200°–210° C for 5 hours reaching a maximum pressure of 1800 psi which decreased over 5 hours to 1200 psi. The final pressure at ambient temperature was 350 psi. After venting the residual pressure, the composition of the product was analyzed by vapor phase chromatography. The product composition is given in Table I, supra.

EXAMPLE 3

Into a 300 ml high pressure reaction vessel were charged 50.0 g. (0.25 mole) γ-cyanopropylmethyldiethoxysilane and 22.3 g of 5.61 wt% $CoS_3$ in ethanol (1.25 g of $CoS_3$). The molar ratio of nitrile to catalyst was 31:1. The vessel was sealed, chilled and 8.5 g (0.25 mole) of $H_2S$ admitted. The reactor was then pressurized to 900 psi (approx. 0.55 mole) with hydrogen. The vessel was heated to 200–210° with agitation for 5 hours reaching a maximum pressure of 2075 psi and decreasing after 5 hours to 1850 psi. The final pressure at ambient temperature was 800 psi. After venting the residual pressure, the product composition was analyzed by vapor phase chromatography. The product composition is given in Table I, supra.

EXAMPLE 4 (Control Experiment)

Into a 300 ml high pressure reaction vessel were charged 9.5 g (0.23 mole) of acetonitrile and 22.3 g. of 5.6 wt% $CoS_3$/NaCl in ethanol (8.0 millimoles of $CoS_3$). The molar ratio of nitrile to catalyst = 29:1. The reaction vessel was sealed, cooled to Dry Ice temperature, and 8.5 g (0.25 mole) of hydrogen sulfide was added by means of a calibrated metering system. The reactor was then pressurized to 850 psi (approx. 0.6 mole) with hydrogen. The vessel was heated to 200°–210° C for 5 hours in a shaker assembly, achieving a maximum pressure of 1800 psi before dropping to 1500 psi. The final pressure at ambient temperature was 450 psi. After venting the residual pressure, the product composition was analyzed by vapor phase chromatography. The product composition is given in Table I, supra.

EXAMPLE 5

Into a 300 ml. high pressure reactor were charged 81 grams β-cyanoethyltriethoxysilane, 12 grams of sulfur and 2.3 grams of cobalt polysulfide (composition approximate $CoS*_{2.8}$). The contents were heated at 200° C. and pressurized with 1800 p.s.i.g. of hydrogen gas. After 5 hours, the reaction was stopped. Excess gas was vented. A total of 90 grams of crude reaction product was collected. Vapor phase chromatographic analysis showed 87% yield of $(EtO)_3Si(CH_2)_3SH$ and about 3% yield of $[(EtO)_2Si\ CH_2CH_2CH_2SH]_2O$. Distillation of the crude product yielded a fraction having a boiling point of 58° C. at 2 mm Hg. The yield of $(EtO)_3Si\ CH_2CH_2CH_2SH$, based on distillation data, was 82%. The distilled product was identified by its boiling point and IR spectrum in comparison with an authentic sample. "Et" in this example means ethyl.

*Made by method of M. W. Farlow et al., Industrial and Engineering Chemistry, Vol. 42, pp. 25–47 (1950).

EXAMPLE 6

Into a 300 ml. rocking autoclave were charged 76.4 grams (0.35 mole) of $(EtO)_3SiCH_2CH_2CN$ (beta-cyanoethyltriethoxysilane), 11.3 grams of sulfur and 2 grams of nickel polysulfide catalyst** in toluene to form 7.35 grams of a paste. The reactor was flushed with dry nitrogen and then charged with 1700 p.s.i.g. of hydrogen gas. The contents were heated to 200° C for 5 hours. It was then cooled to room temperature. Excess gas was vented and the crude reaction mixture was collected. Analysis of The reaction mixture showed 80% yield of $(EtO)_3Si\ CH_2CH_2CH_2SH$ in about 70% conversion. Et means ethyl.

**M. W. Farlow et al., supra.

EXAMPLE 7

Reductive thiolation of β-cyanoethylethoxysilane with sulfur, cobalt polysulfide catalyst and low hydrogen pressure.

Into a 300 ml. high pressure reactor were charged 72.4 grams β-cyanoethyltriethoxysilane, 10.7 grams sulfur and 2.1 grams cobalt polysulfide. The contents were heated to 200° C. and pressurized with a constant 750 p.s.i.g. of hydrogen gas. After 5 hours of heating, the reaction was stopped. Excess gas was vented and the dark brown reaction mixture was collected. The reaction mixture was analyzed by vapor phase chromatography (VPC). Results of the VPC analysis showed approximately 50% yield of tetraethylorthosilicate, $Si(OEt)_4$, and 15.6% yield of the mercaptan, $(EtO)_3SiCH_2CH_2CH_2SH$. The $Si(OEt)_4$ formed in the side reaction was isolated by fractional distillation and was identified by infrared and nuclear magnetic resonance spectroscopy. Et in this example means ethyl.

EXAMPLE 8

Reductive thiolation of β-cyanoethyltriethoxysilane with sulfur, cobalt polysulfide and rhenium heptasulfide catalysts at low hydrogen pressure.

Into a 300 ml. high pressure reactor were charged 72.4 grams (0.333 mole) of β-cyanoethyltriethoxysilane, 10.7 grams (0.333 gram-atom) of sulfur, 2.1 grams cobalt polysulfide and 0.15 gram of rhenium heptasulfide as a cocatalyst. The reaction was carried out at 200° C. for 8 hours at a constant input of hydrogen gas at 750 p.s.i.g. Vapor phase chromatographic analysis of the reaction mixture at the end of 8 hours showed that the tetraethylorthosilicate, $Si(OEt)_4$, yield was very low (about 2 to 3%). The yield of $(EtO)_3SiCH_2CH_2CH_2SH$ was excellent (better than 90%), although the conversion of $(EtO)_3SiCH_2CH_2CN$ (about 50%) was somewhat lower than the same reaction carried out at much higher hydrogen pressure (over 1500 p.s.i.g.). The significance of the rhenium heptasulfide cocatalyst was that the side product, tetraethylorthosilicate, was reduced to an insignificantly low level in comparison with the same reaction carried out in the absence of rhenium heptasulfide cocatalyst (see Example 5). Et employed in this example means ethyl.

EXAMPLE 9

Reductive thiolation of beta-cyanoethyltriethoxysilane with hydrogen sulfide and cobalt polysulfide catalyst at low hydrogen pressure.

Into a 300 ml. high pressure reactor were charged 72.4 grams (0.333 mole) of beta-cyanoethyltriethoxysilane and 2.1 grams of cobalt polysulfide catalyst. The reactor was cooled with a dry-ice/acetone bath and 14.2 grams of hydrogen sulfide (0.417 mole) were condensed into the reactor. The reactor was charged with 750 p.s.i.g. of hydrogen gas at about room temperature. The contents were then heated to 200° C. for a total of 6 hours. Unreacted $H_2S$ was vented. The reaction product was collected in a bottle. Vapor phase chromatographic analysis of the reaction mixture showed very low yield of tetraethylorthosilicate, $Si(OEt)_4$, (about 2 to 3 percent). Yield of the mercaptan, $(EtO)_3SiCH_2CH_2CH_2SH$, was excellent (90%) and conversion of starting material, $(EtO)_3SiCH_2CH_2CN$, to products was 70%. Et in this example means ethyl.

What is claimed is:

1. The process of reducing $\beta$-cyanoethyltrialkoxysilane to mercaptopropyltrialkoxysilane which comprises reacting said cyanoethyltrialkyloxysilane at a temperature between about 50° C and about 300° C with sulfur and hydrogen in the ratio of at least 3 moles of hydrogen for each mole of the silane and at least one mole of sulfur for each mole of the silane, in the presence of about 0.001 to about 10 weight percent based on the weight of the silane, sulfur and hydrogen, of a sulfide or polysulfide of a transition metal consisting of cobalt, nickel, titanium, rhenium and molybdenum.

* * * * *